US008940056B2

(12) United States Patent
Li

(10) Patent No.: US 8,940,056 B2
(45) Date of Patent: *Jan. 27, 2015

(54) URETERAL STENTS FOR RELEASE OF UROLOGICALLY BENEFICIAL AGENTS

(75) Inventor: Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 340 days.

This patent is subject to a terminal disclaimer.

(21) Appl. No.: 13/242,105

(22) Filed: Sep. 23, 2011

(65) Prior Publication Data

US 2012/0016490 A1  Jan. 19, 2012

Related U.S. Application Data

(63) Continuation of application No. 12/411,492, filed on Mar. 26, 2009, now Pat. No. 8,048,171.

(60) Provisional application No. 61/072,076, filed on Mar. 27, 2008.

(51) Int. Cl.
| | | |
|---|---|---|
| *A61F 2/04* | (2013.01) | |
| *A61M 27/00* | (2006.01) | |
| *A61F 2/94* | (2013.01) | |

(52) U.S. Cl.
CPC .......... *A61M 27/008* (2013.01); *A61M 27/002* (2013.01); *A61F 2/04* (2013.01); *A61F 2/94* (2013.01); *A61M 2210/1078* (2013.01); *A61M 2210/1082* (2013.01); *A61M 2210/1085* (2013.01)
USPC ...................................... 623/23.66

(58) Field of Classification Search
CPC ............ A61M 27/002; A61M 27/008; A61M 2210/1085; A61M 2210/1078; A61M 2210/1082; A61F 2002/048
USPC ................... 623/23.64–23.66, 23.7; 604/8–9
See application file for complete search history.

(56) References Cited

U.S. PATENT DOCUMENTS

| | | |
|---|---|---|
| 4,131,731 A | 12/1978 | Lai et al. |
| 5,580,924 A | 12/1996 | Wildi et al. |
| 5,622,665 A | 4/1997 | Wang |
| 6,379,382 B1 | 4/2002 | Yang |
| 6,508,805 B1 | 1/2003 | Garabedian et al. |
| 6,545,097 B2 | 4/2003 | Pinchuk et al. |

(Continued)

FOREIGN PATENT DOCUMENTS

| | | |
|---|---|---|
| WO | 2005/094930 A1 | 10/2005 |
| WO | 2006/121969 A1 | 11/2006 |

(Continued)

*Primary Examiner* — Andrew Iwamaye
(74) *Attorney, Agent, or Firm* — Kacvinsky Daisak Bluni PLLC

(57) ABSTRACT

According to one aspect of the invention, ureteral stents are provided that comprise an elongated stent body and a urologically beneficial agent. The elongated stent body comprises a kidney portion adapted to occupy the kidney of a subject upon implantation, a ureter portion adapted to occupy the ureter of a subject upon implantation, and a bladder portion adapted to occupy the bladder of a subject upon implantation. The ureteral stents of the invention are adapted to release the urologically beneficial agent into the subject. Moreover, the amount of urologically beneficial agent that is released varies along the length of the stent. Other aspects of the invention pertain to methods of forming such stents and methods of using such stents.

22 Claims, 3 Drawing Sheets

(56) References Cited

U.S. PATENT DOCUMENTS

| | | |
|---|---|---|
| 6,764,505 B1 | 7/2004 | Hossainy et al. |
| 7,288,084 B2 | 10/2007 | Li |
| 7,291,165 B2 | 11/2007 | Rosenthal et al. |
| 7,445,642 B2 | 11/2008 | Amos et al. |
| 7,666,223 B2 | 2/2010 | Santos et al. |
| 7,862,552 B2 | 1/2011 | McIntyre et al. |
| 8,048,171 B2 * | 11/2011 | Li .............................. 623/23.66 |
| 2003/0018306 A1 | 1/2003 | Bucay-Couto et al. |
| 2003/0100830 A1 | 5/2003 | Zhong et al. |
| 2003/0153983 A1 | 8/2003 | Miller et al. |
| 2003/0224033 A1 | 12/2003 | Li et al. |
| 2004/0022824 A1 | 2/2004 | Li et al. |
| 2004/0131863 A1 | 7/2004 | Belliveau |
| 2004/0249441 A1 | 12/2004 | Miller et al. |
| 2005/0234388 A1 * | 10/2005 | Amos et al. ........................ 604/8 |
| 2005/0271698 A1 | 12/2005 | Bucay-Couto et al. |
| 2006/0100695 A1 | 5/2006 | Peacock et al. |
| 2006/0264912 A1 | 11/2006 | McIntyre et al. |
| 2007/0078446 A1 | 4/2007 | Lavelle |
| 2007/0161967 A1 | 7/2007 | Fischer et al. |
| 2007/0298069 A1 | 12/2007 | Li et al. |
| 2008/0102098 A1 | 5/2008 | Dave et al. |
| 2008/0167710 A1 | 7/2008 | Dave et al. |

FOREIGN PATENT DOCUMENTS

| | | |
|---|---|---|
| WO | 2007/149184 A1 | 12/2007 |
| WO | 2008/002434 A2 | 1/2008 |

\* cited by examiner

URETERAL STENTS FOR RELEASE OF UROLOGICALLY BENEFICIAL AGENTS

STATEMENT OF RELATED APPLICATION

This application is a continuation of U.S. patent application Ser. No. 12/411,492, filed Mar. 26, 2009, now U.S. Pat. No. 8,048,171, issued Nov. 1, 2011, entitled "Ureteral Stents For Release of Urologically Beneficial Agents," which claims the benefit of U.S. Provisional Patent Application Ser. No. 61/072,076, filed Mar. 27, 2008, entitled "Ureteral Stents For Release Of Urologically Beneficial Agents," both of which applications are incorporated by reference herein in their entirety.

FIELD OF THE INVENTION

The present invention relates generally to ureteral stents, and more particularly to implantable or insertable ureteral stents which release urologically beneficial agents.

BACKGROUND OF THE INVENTION

Ureteral stents are widely used to facilitate drainage in the upper urinary tract (e.g., from the kidney to the bladder), for example, following ureteroscopy, endoureterotomies, and endopyelotomy for ureteral strictures, as well as in other instances where ureteral obstruction may occur for example, following lithotripsy. Such stents, however, are commonly associated with pain and discomfort in the bladder and flank area after insertion. One way to minimize pain and discomfort is to orally administer drugs to the patient. Commonly prescribed oral drugs are opioid analgesia (e.g. Vicodin® and Percocet®), which are controlled substances and have the potential for abuse by patients.

Another way to address pain and discomfort is to release a therapeutic agent from the ureteral stent. See Pub. Nos. US 2003/0224033 to Li et al. and US 2006/0264912 to McIntyre et al.

Another way of addressing this pain is to use a softer material, particularly in forming the proximal end of the stent, which engages more sensitive tissue in the bladder region. Stents of this type may employ co-extrusion to combine a firm durometer EVA copolymer at the distal end, which improves stent advancement, and a soft durometer EVA at the proximal end, which improves comfort. A specific example of such a stent is the Polaris™ Dual Durometer Percuflex® Ureteral Stent with HydroPlus™ Coating, Boston Scientific, Natick, Mass., USA.

SUMMARY OF THE INVENTION

According to one aspect of the invention, ureteral stents are provided that comprise an elongated stent body and a urologically beneficial agent. The elongated stent body comprises a kidney portion adapted to occupy the kidney of a subject upon implantation, a ureter portion adapted to occupy the ureter of a subject upon implantation, and a bladder portion adapted to occupy the bladder of a subject upon implantation. The ureteral stents of the invention are adapted to release the urologically beneficial agent into the subject. Moreover, the amount of urologically beneficial agent that is released varies along the length of the stent, for example, by varying the amount of the loaded urologically beneficial agent along the length of the stent.

Other aspects of the invention pertain to methods of forming such stents and methods of using such stents.

These and other aspects, as well as various embodiments and advantages of the present invention will become immediately apparent to those of ordinary skill in the art upon review of the Detailed Description and any claims to follow.

DETAILED DESCRIPTION OF THE INVENTION

Figure 1:
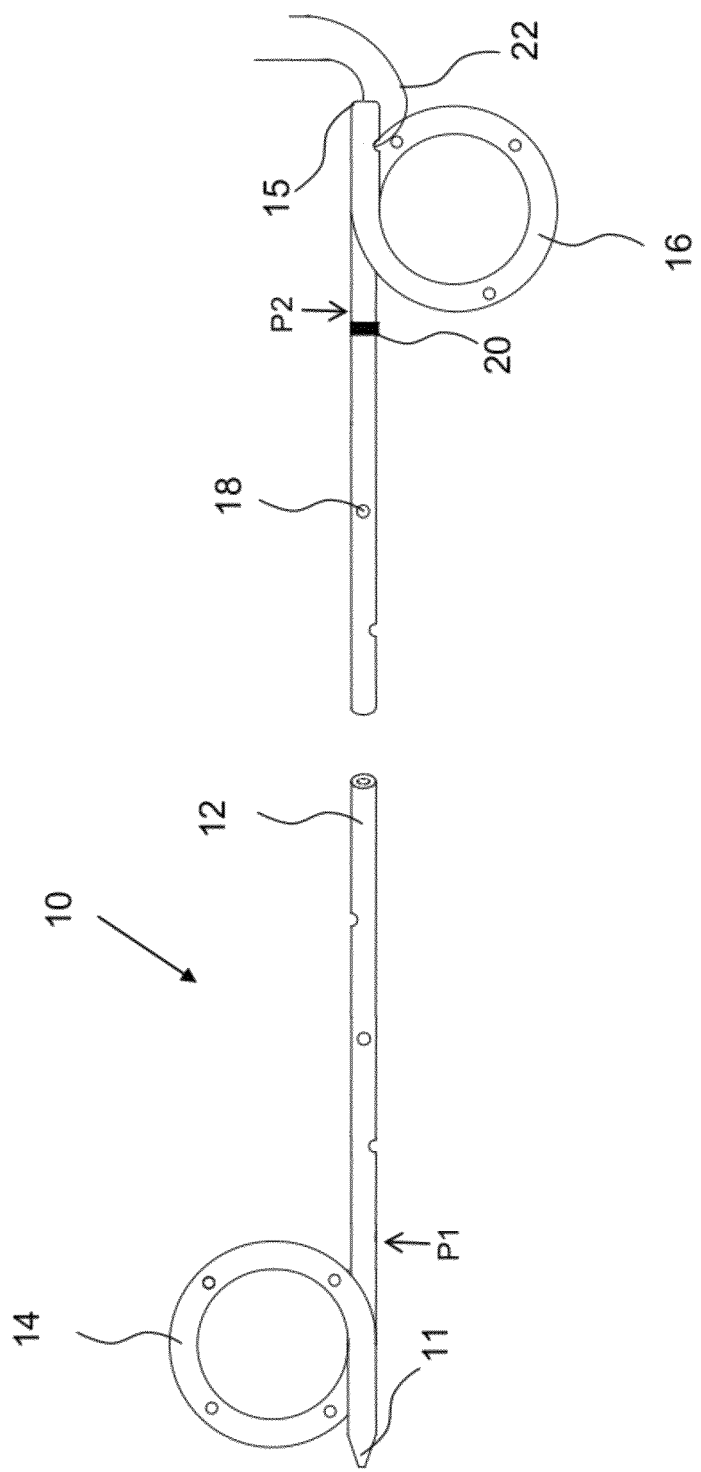
FIG. 1 is a side view of a ureteral stent, in accordance with an embodiment of the invention.

A more complete understanding of the present invention is available by reference to the following detailed description of numerous aspects and embodiments of the invention. The detailed description of the invention which follows is intended to illustrate but not limit the invention.

In one aspect, the present invention provides ureteral stents, which are adapted to release one or more urologically beneficial agents in pharmaceutically effective amounts. For example, such agents may be provided in amounts effective to achieve the following benefits, among others: (a) the relief of pain and/or discomfort associated with the ureteral stent and (b) treatment of a disease or condition associated with the kidney, ureter and/or bladder, such as cancer, among others. As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

The ureteral stents of the invention comprise an elongated stent body and a urologically beneficial agent which is released from the stent. The elongated stent body comprises a kidney portion adapted to occupy the kidney of a subject upon implantation, a ureter portion adapted to occupy the ureter of a subject upon implantation, and a bladder portion adapted to occupy the bladder of a subject upon implantation. Moreover, the ureteral stents of the invention (i.e., the entire stent or at least a portion of the stent) are adapted to release the urologically beneficial agent into the subject. The urologically beneficial agent is not, however, evenly released along the length of the ureteral stent, for example, as a result of non-uniform agent loading along the length of the stent.

Drug release may be assessed using in vitro techniques. For example, release from the kidney portion, the ureter portion, and the bladder portion of the stent can be independently assessed by measuring flow-through release by each of these portions into artificial urine (AU), such as that detailed in the British Standard for simulated/artificial urine formulation, at a flow rate of 0.5 ml/min. For this purpose, the stent portion may be placed inside a piece of tygon tubing which is connected to a peristaltic pump to deliver the AU media. The tubing and stent are submerged in a 37° C. water bath to simulate body temp. Release is measured over time.

In some embodiments, at least 50% of the cumulative total release of urologically beneficial agent that occurs from the stent during the first 7 days of implantation (e.g., at least 50%, at least 75%, at least 90%, at least 95%, at least 97.5%, at least 99%, or even 100%) is released from the kidney portion of the stent. In certain embodiments, this will mean that at least 50% of the total urologically beneficial agent that is loaded within the entire ureteral stent (e.g., at least 50%, at least 75%, at least 90%, at least 95%, at least 97.5%, at least 99%, or even 100%) is located in the kidney portion of the stent. Such embodiments may be desirable, for example, where the urologically beneficial agent is a pain/discomfort relieving agent and where the kidney and/or upper ureter is the primary source of pain/discomfort.

Thus, in some embodiments, the kidney portion, which may constitute, for example, 10-20% of the length of the stent, has a higher cumulative total release of urologically beneficial agent during the first 7 days of implantation, than does the remainder of the stent, including the ureter portion, which may, for example, constitute 60-80% of the length of the stent, and the bladder portion, which may, for example, constitute 10-20% of the length of the stent.

In some embodiments, the amount of urologically beneficial agent located in the kidney portion may be at least two times the amount of urologically beneficial agent located in the ureter portion (e.g., at least 2 times, at least 4 times, at least 10 times, or more, including an infinite number of times where there is no agent in the ureter portion at all).

Figure 3:
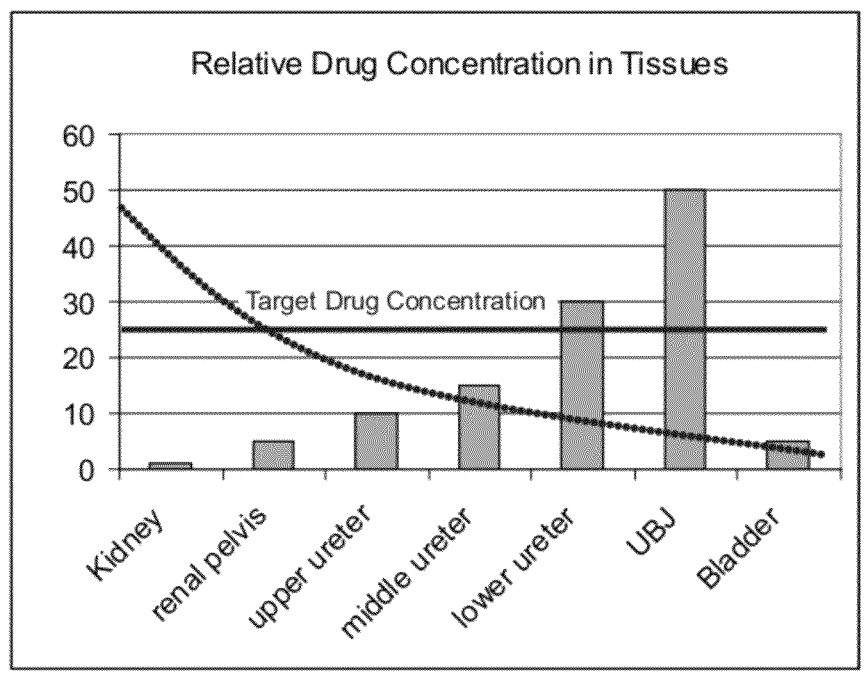
FIG. 3 is a bar graph showing relative concentrations of urologically beneficial agent distributed along the urinary tract when the agent is released from a ureteral stent uniformly loaded with the agent.

FIG. 3 is a bar graph, based on an animal study, which shows the relative concentration of a urologically beneficial agent distributed along the urinary tract (i.e., kidney; renal pelvis; upper ureter; middle ureter; lower ureter; the junction between the ureter and bladder (UBJ) also known as the uterovesical junction; and bladder) when the urologically beneficial agent is released from a ureteral stent that is uniformly loaded with the agent. The non-uniform agent distribution throughout the urinary tissue is believed to be the result of non-uniform drug concentration inside the urinary tract, which is lowest in the kidney end and highest right before the uterovesical junction. For embodiments where the urologically beneficial agent is used for the relief of pain and/or discomfort associated with the ureteral stent, the blue lines of FIG. 3 indicate two possible idealized agent distributions, assuming the entire ureter (solid blue line) or the upper ureter (dotted blue line) is the cause for pain and discomfort.

As seen from FIG. 3, in the case of a ureteral stent having an even distribution of a urologically beneficial agent along its length, the concentration of released agent measured in bladder tissue is approximately 5 times that measured in kidney tissue, while the concentration of released agent measured in ureter tissue is, on average, approximately 15 times that measured in the kidney tissue (although the concentration varies dramatically along the length of the ureter). Without wishing to be bound by theory, it is believed that as the urine travels from the kidney along the ureter, the concentration of urologically beneficial agent in the urine increases due to increased exposure of the urine to the stent. Once the urine enters the bladder, however, it is diluted by urine traveling from the other ureter. Therefore, the drug concentration in the urine inside the ureter is non-uniform, ranging from near-zero in the kidney end and reaching its maximum immediately before it discharges into the bladder.

As previously indicated, in some embodiments, up to 100% of the release is from the kidney portion of the stent. With such a design, the concentration of urologically beneficial agent may be highest in the kidney portion of the ureter, intermediate in the middle portion of the ureter and lowest in the bladder portion of the ureter. This is illustrated in an idealized fashion by the dotted line in FIG. 3, assuming tissue adsorption of the urologically beneficial agent is relatively large compared that released. Where tissue adsorption of the agent is relatively small compared that released, such a design will provide a drug concentration in an upper portion of the urinary tract (e.g., lower kidney, renal pelvis, the entire length of the ureter) that is relatively constant. These embodiments may be desirable, for example, where the urologically beneficial agent is a pain/discomfort relieving agent and wherein the kidney and/or upper ureter is the primary source of the pain/discomfort.

In some embodiments, while the majority of the release is from the kidney portion, a small amount of release is form the ureter portion, so as to maintain the concentration urologically beneficial along the length of the ureter (as illustrated in an idealized fashion by the solid line in FIG. 3), even as agent is being absorbed by adjacent tissue. This embodiment is desirable, for example, where the urologically beneficial agent is a pain/discomfort relieving agent and wherein the entire ureter is a source of pain/discomfort and/or where the agent is absorbed by the local tissues in substantial amounts.

In some embodiments, the release from the kidney portion is at least 2 times that from the bladder portion (e.g., at least 2 times, at least 4 times, at least 10 times, or more, including an infinite number of times where there is no release from the bladder portion at all), for example, because the amount of agent that is loaded in kidney portion is at least two times the amount loaded in the bladder portion.

In some embodiments, the release from the bladder portion is at least 2 times that from the ureter portion (e.g., at least 2 times, at least 4 times, at least 10 times, or more, including an infinite number of times where there is no release from the ureter portion at all), for example, because the amount of agent that is loaded in bladder portion is at least two times the amount loaded in the ureter portion.

Thus, in some embodiments, the release is highest from the kidney portion of the stent, lowest from the ureter portion of the stent (including zero release), and intermediate from the bladder portion of the stent. For example, in some embodiments, the release from the bladder portion is at least two times that from the ureter portion, while the release from the kidney portion is at least two times that from the bladder portion (e.g., because the amount of agent that is loaded in kidney portion is at least two times the amount loaded in the bladder portion, which in turn is at least two times the amount loaded in the ureter portion).

In various embodiments, for instance, embodiments where the at least one urologically beneficial agent is released from a polymeric carrier region as discussed below, the concentration of urologically beneficial agent may be varied along the length of the ureteral stent (e.g., to cause preferential release from certain portions of the stent relative to others). For example, the concentration can be highest in the kidney portion of the stent, lowest in the ureter portion of the stent, and intermediate in the bladder portion of the stent. (e.g., the concentration in the bladder portion may be at least two times that of the ureter portion, while the concentration in the kidney portion is at least two times that in the bladder portion, such that the concentration in the kidney portion is at least four times that of the ureter portion).

As also seen from FIG. 3, the reduction in agent concentration between the uterovesical junction and the bladder is about 10 times, even though the urologically beneficial agent is released along the entire length of the stent. In some embodiments (e.g., where the urologically beneficial agent is a pain/discomfort relieving agent and the bladder is a significant source of the pain/discomfort), the amount of urologically beneficial agent released from the bladder pigtail is as high as or higher than from the kidney pigtail. For example, in some embodiments, at least 50% (e.g., at least 50% at least 75%, at least 90%, at least 95%, at least 97.5%, at least 99%, or even 100%) of the cumulative total release of urologically beneficial agent that occurs during the first 7 days of implantation may be released from the bladder portion of the stent, meaning that at most 50% (e.g., at most 50%, at most 25%, at most 10%, at most 5%, at most 2.5%, at most 1%, or even 0%) of the cumulative total release of urologically beneficial agent that occurs during the first 7 days of implantation may be released from the kidney portion of the stent. In various embodiments, this will mean that at least 50% of the total amount of urologically beneficial agent present in the device is loaded in the bladder portion of the stent, while at most 50% is loaded in the kidney portion.

In some aspects, the urologically beneficial agent loaded in the bladder portion may be different from the urologically beneficial agent loaded into the kidney portion. For example, one urologically beneficial agent may be loaded into the kidney portion of the stent to address stent pain and discomfort, while another urologically beneficial agent is loaded into the bladder portion of the stent to address infection and/or biofilm formation, or even for treatment of bladder cancer.

In some embodiments, for instance, embodiments where the at least one urologically beneficial agent is released from a polymeric carrier region as discussed below, the polymer composition may be varied along the length of the ureteral stent (e.g., to create preferential release in certain portions of the stent). For instance, different polymers may be employed in differing portions of the stent, the ratio of two or more different polymers in a polymer blend may be varied along the length of the stent, the ratio of two or more different monomers in a copolymer may be varied along the length of the stent, and so forth.

In some embodiments, the ureteral stent is provided with one or more retention elements. For example, the stent may take on a particular beneficial shape in vivo, for example, immediately upon removal of a guide wire and/or emergence from a channel (e.g., due to elastic rebound of the material) or upon activation by a physician. For example, the device may take on a non-linear form such as a coiled configuration. Such constructions allow the ureteral stent to be held in place in the urinary tract, for example, by forming a coil or other retention element in the kidney (e.g., in the renal calyx and/or renal pelvis), the bladder, or both. Other examples of retention elements include corkscrews, mallincotts, barbs, mushrooms, and hook ends, among others.

Figure 2:
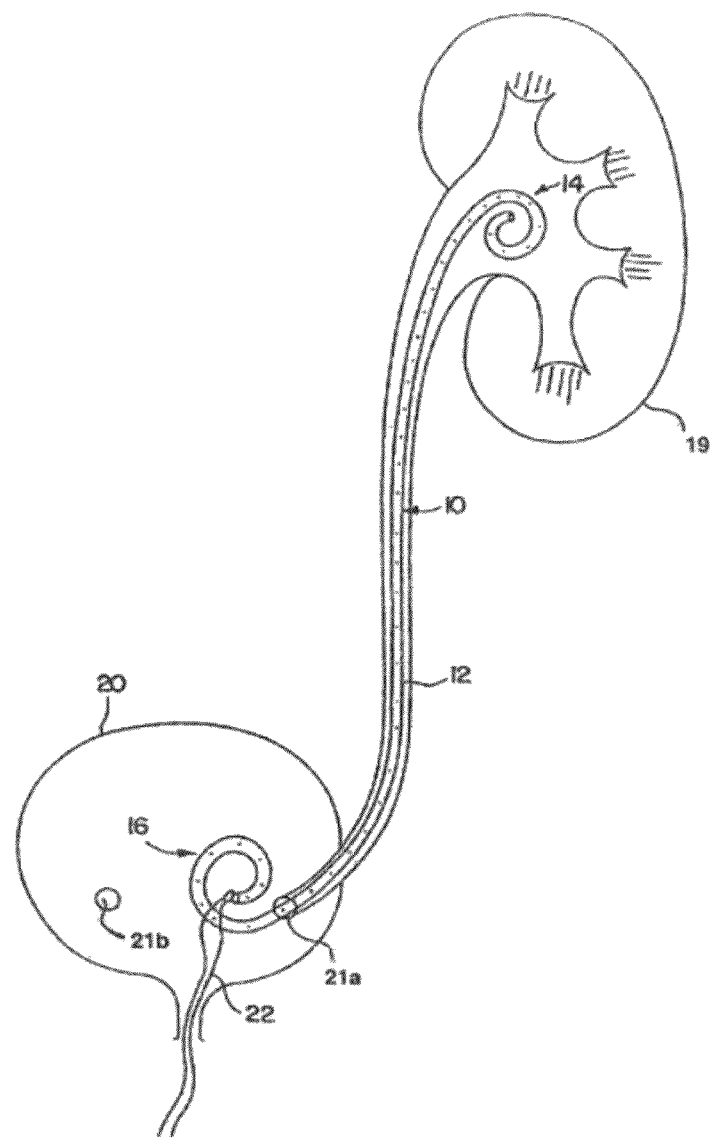
FIG. 2 shows the ureteral stent of FIG. 1 as positioned within the body.

A schematic diagram of a stent 10 in accordance with one specific embodiment of the invention is illustrated in FIG. 1. The stent 10 comprises an elongated stent body in the form of a tubular polymeric extrusion including a renal coil 14, bladder coil 16, and a substantially linear shaft 12 (most or all of which occupies the ureter upon implantation) between the coils 14, 16. The stent 10 shown is further provided with the following: (a) a tapered distal tip 11, to aid insertion, (b) multiple side ports 18 (one numbered), which are arranged in a spiral pattern along the length of the stent body to promote drainage, (c) graduation marks 20 (one illustrated), which are used for visualization by the physician to know when the appropriate length of stent has been inserted into the ureter, and (d) a Nylon suture 22, which aids in positioning and withdrawal of the stent, is provided at the proximal end 15 of the stent, as is known in that art. The stent 10 also comprises a urologically beneficial agent, the majority of which is in the portion of the stent extending from position P1 to the distal tip 11 of the stent 10. For example, in certain embodiments, a highest concentration of urologically beneficial agent is provided within the stent between position P1 and the distal tip 11, a lowest concentration of urologically beneficial agent is provided within the stent between position P1 and position P2, and an intermediate concentration of urologically beneficial agent is provided within the stent between position P2 and the proximal (bladder) end 15. During placement, the ureteral stent 10 may be placed over a urology guide wire, through a cystoscope and advanced into position with a positioner. Once the distal (kidney) end of the stent is advanced into the kidney, the guide wire is removed, allowing the coils 14, 16 to form in the kidney 19 and bladder 20, as shown in FIG. 2. As shown in FIG. 2, the stent 10 extends through the ureteral orifice 21a and into the bladder 20. For clarity, the ureter entering bladder 20 through the opposite ureteral orifice 21b is not shown.

As used herein, a "urologically beneficial agent" is an agent that is sufficiently safe and effective for use in humans or animals when released from an implantable or insertable urological device, in particular, a ureteral stent. Urologically beneficial agents include agents that benefit the urinary tract and agents that reduce side effects associated with ureteral stents, including pain or discomfort and infection, among other side effects.

In some embodiments, urologically beneficial agents for use in the invention have one or more of the following, among others: muscle relaxant activity (e.g., they have musculotropic relaxant properties, smooth muscle relaxant properties, etc.), anti-spasmodic activity, anti-inflammatory activity, analgesic activity, anti-cancer activity and anti-microbial activity.

Urologically beneficial agents for use in the invention may be selected, for example, from one or more suitable members of the following, among others: alpha-adrenergic blockers, calcium channel blockers, beta-adrenergic agonists, bronchodilators, nitric oxide donors, nitric oxide releasing compounds, prostaglandins, corticosteroids, narcotic analgesic agents, non-narcotic analgesic agents, local anesthetic agents, antiproliferative agents and antineoplastic agents, among others, as well as combinations thereof.

Examples of alpha-adrenergic blockers for use in the present invention may be selected from suitable members of the following: alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine, among others, as well as combinations and pharmaceutically acceptable salts, esters and other derivatives of the same. Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Examples of calcium channel blockers for use in the present invention may be selected from suitable members of the following: arylalkylamines (including phenylalkylamines) such as verapamil, gallopamil, bepridil, clentiazen, fendiline, mibefradil, prenylamine, semotiadil, and terodiline, benzothiazepines such as diltiazem; dihydropyridine derivatives (including 1,4-dihydropyridine derivatives) such as amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine and nitrendipine, piperazine derivatives such as cinnarizine, dotarizine, flunarizine, lidoflazine and lomerizine, calcium channel blockers such as bencyclane, etafenone, fantofarone, monatepil and perhexyline, among other calcium channel blockers, as well as combinations and pharmaceutically acceptable salts, esters and other derivatives of the same.

Examples of beta-adrenergic agonists for use in the present invention may be selected from suitable members of the following: albuterol, bambuterol, bitolterol, carbuterol, clenbuterol, clorprenaline, denopamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, salmerterol, soterenol, terbutaline, tretoquinol, tulobuterol and xamoterol, among others, as well as combinations and pharmaceutically acceptable salts, esters and other derivatives of the same.

Examples of bronchodilators for use in the present invention may be selected from suitable members of the following: (a) ephedrine derivatives such as albuterol, bambuterol, bitolterol, carbuterol, clenbuterol, clorprenaline, dioxethedrine, ephedrine, epinephrine, eprozinol, etafedrine, ethylnorepinephrine, fenoterol, formoterol, hexoprenaline, isoetharine, isoproterenol, mabuterol, metaproterenol, n-methylephedrine, pirbuterol, procaterol, protokylol, reproterol, rimiterol, salmeterol, soterenol, terbutaline and tulobuterol, (b) quaternary ammonium compounds such as bevonium methyl sulfate, flutropium bromide, ipratropium bromide, oxitropium bromide and tiotropium bromide, (c) xanthine derivatives such as acefylline, acefylline piperazine, ambuphylline, aminophylline, bamifylline, choline theophyllinate, doxofylline, dyphylline, etamiphyllin, etofylline, guaithylline, proxyphylline, theobromine, 1-theobromineacetic acid and theophylline, and (d) other bronchodilators such as fenspiride, medibazine, methoxyphenanime and tretoquinol, among others, as well as combinations and pharmaceutically acceptable salts, esters and other derivatives of the forgoing.

Examples of nitric oxide donors/releasing molecules for use in the present invention may be selected from suitable members of the following: inorganic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, among others, as well as pharmaceutically acceptable salts, esters and other derivatives of the same, and combinations of the foregoing.

Examples of prostaglandins and analogs thereof for use in the present invention may be selected from suitable members of the following: prostaglandins such as PGE1 and PGI2 and prostacyclin analogs such as ciprostene, epoprostenol, carbacyclin, iloprost and beraprost, among others, as well as pharmaceutically acceptable salts, esters and other derivatives of the same, and combinations of the foregoing.

Examples of corticosteroids for use in the present invention may be selected from suitable members of the following: betamethasone, cortisone, dexamethasone, deflazacort, hydrocortisone, methylprednisolone, prednisolone, prednisone and triamcinolone, among others, as well as combinations and pharmaceutically acceptable salts, esters and other derivatives of the same.

Examples of narcotic analgesic agents for use in the present invention may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present invention may be selected from suitable members of the following: analgesic agents such as acetaminophen, and non-steroidal anti-inflammatory drugs such as aspirin, diflunisal, salsalate, ibuprofen, ketoprofen, naproxen indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present invention may be selected from suitable members of the following: benzocaine, cocaine, lidocaine, mepivacaine, and novacaine, among others, as well as combinations and pharmaceutically acceptable salts, esters and other derivatives of the same.

Examples of antiproliferative/antineoplastic agents for use in the present invention may be selected from suitable members of the following: antimetabolites such as purine analogs (e.g., 6-mercaptopurine or cladribine, which is a chlorinated purine nucleoside analog, etc.), pyrimidine analogs (e.g., cytarabine, 5-fluorouracil, etc.) and methotrexate, nitrogen mustards, alkyl sulfonates, ethylenimines, antibiotics (e.g., daunorubicin, doxorubicin, etc.), nitrosoureas, cisplatin, agents affecting microtubule dynamics (e.g., vinblastine, vincristine, colchicine, Epo D, paclitaxel, epothilone, etc.), caspase activators, proteasome inhibitors, angiogenesis inhibitors (e.g., endostatin, angiostatin, squalamine, etc.), olimus family drugs (e.g., sirolimus, everolimus, tacrolimus, zotarolimus, etc.), cerivastatin, flavopiridol and suramin, among others, as well as combinations and pharmaceutically acceptable salts, esters and other derivatives of the same.

Many of the above and other urologically beneficial agents may be found, for example, in *The Merck Index*, 13$^{th}$ Edition, M. J. O'Neil, Senior Editor, published by Merck Research Laboratories, 2001.

Examples of antimicrobial agents for use in the present invention may be selected, for example, from triclosan, chlorhexidine, nitrofurazone, benzalkonium chlorides, silver salts, silver particles, metallic silver and antibiotics, such as rifampin, gentamicin and minocycline, and combinations thereof, among others.

Ureteral stents in accordance with the invention may also contain various optional supplemental agents, including imaging agents.

For example, x-ray based fluoroscopy is a diagnostic imaging technique that allows real-time patient monitoring of motion within a patient. To be fluoroscopically visible, devices and/or compositions are typically rendered more absorptive of x-rays than the surrounding tissue (e.g., radiopaque materials). In various embodiments of the invention, this is accomplished by the use of contrast agents. Examples of contrast agents for use in connection with x-ray fluoroscopy include metals, metal salts and oxides (particularly bismuth salts and oxides), and iodinated compounds, among others. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others.

Ultrasound uses high frequency sound waves to create an image of living tissue. A sound signal is sent out, and the reflected ultrasonic energy, or "echoes," are used to create the image. Ultrasound imaging contrast agents are materials that enhance the image produced by ultrasound equipment. Ultrasonic imaging contrast agents can be, for example, echogenic (i.e., materials that result in an increase in the reflected ultrasonic energy) or echolucent (i.e., materials that result in a decrease in the reflected ultrasonic energy). Suitable ultrasonic imaging contrast agents for use in connection with the present invention include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid), among others. Microbubbles can also be used as ultrasonic imaging contrast agents, as is known in the imaging art.

Magnetic resonance imaging (MRI) produces images by differentiating detectable magnetic species in the portion of the body being imaged. In the case of $^1$H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and thereby allow for enhanced contrast and better images of the area of interest. For contrast-enhanced MRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest. Further information can be found, for example, in U.S. Patent Application No. 2003/0100830 entitled "Implantable or insertable medical devices visible under magnetic resonance imaging."

As used herein, a "polymeric region" is a region (e.g., corresponding to an entire stent body or to portion of a stent body) that contains one or more types of polymers. As used herein, a "carrier region" is a region that contains one or more agents, for example, selected from urologically beneficial agents and optional supplemental agents such as the imaging agents described above, among others. As used herein, a "polymeric carrier region" is a region that contains one or more polymers and one or more agents. The one or more agents may or may not be released from the polymeric carrier region. (For instance, while it may be desirable to release a urologically beneficial agent, it may be undesirable to release an imaging agent.)

The polymeric carrier region may correspond, for example, to one or more of the following regions, among others: an entire ureteral stent body, a monolithic segment corresponding to a portion of the length of a ureteral stent body (e.g., one of a series of annular segments extending along the length of the stent body, which may correspond, e.g., to the kidney portion, the ureter portion, the bladder portion, etc.), one or more polymeric layers extending along the entire length or a portion of the length (e.g., the kidney portion, etc.) of a multilayer ureteral stent body, one or more coating layers (e.g., a layer provided for agent release, but which does not contribute significantly to the mechanical strength of the stent) extending along the entire length or a portion of the length (e.g., the kidney portion, etc.) of a ureteral stent body (e.g., a monolithic stent body, a multilayer stent body, a stent body having multiple monolithic segments extending along its length, etc.), among many other possibilities. Thus, where a urologically beneficial agent is provided in a carrier region, the carrier region may extend along the entire length of the ureteral stent body, or along only a portion of the length of the stent body. Moreover, the concentration of the urologically beneficial agent can vary along the length of the stent body. Furthermore, the polymer composition can vary along the length of the stent body, which may, for example, result in a variation in release rate.

As noted above, a "polymeric" region is one that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used.

Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, for instance an initiator molecule or a linking molecule), comb configurations (e.g., configurations having a main chain and a plurality of side chains), dendritic configurations (e.g., arborescent and hyperbranched polymers), networked (e.g., crosslinked) configurations, and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers. As used herein, "block copolymers" are copolymers that contain two or more polymer blocks that differ in composition, for instance, because a constitutional unit (i.e., monomer) is found in one polymer block that is not found in another polymer block. As used herein, a "polymer block" is a grouping of constitutional units (e.g., 2 to 5 to 10 to 25 to 50 to 100 to 250 to 500 to 1000 or more units). Blocks can be branched or unbranched, and they may be networked (e.g., by crosslinking) Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution.

Polymers for use in the present invention may be selected, for example, from various thermoplastic polymers, elastomeric polymers, and thermoplastic-elastomeric polymers.

Polymers for use in the present invention may be selected, for example, from polycarbonates, silicone polymers, polyurethanes, poly(ether-block-amides), and alkene polymers.

Polycarbonates are derived from the reaction of carbonic acid derivatives with aromatic, aliphatic, or mixed diols. They may be produced, for example, by the reaction of phosgene with a diol in the presence of an appropriate hydrogen chloride receptor or by a melt transesterification reaction between a diol and a carbonate ester. Polycarbonates can be made from a wide variety of starting materials. For example, a common polycarbonate, bisphenol A polycarbonate, is a polycarbonate made by reacting bisphenol A with phosgene by condensation. For further information, see, e.g., U.S. Pat. No. 5,580,924 and the references cited therein.

Silicone polymers (also referred to as polysiloxanes) are polymers comprising one or more types of siloxane units

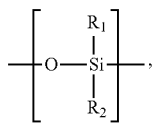

where $R_1$ and $R_2$ can be the same or different and may be selected from linear, branched and cyclic alkyl groups, aromatic groups and alky-aromatic groups, for example, having from 1 to 10 carbon atoms, and having 5 or more, typically 10 to 25 to 50 to 100 to 250 to 500 to 1000 or more siloxane units. Examples include polydimethylsiloxane, polydiethylsiloxane, polymethylethylsiloxane, polymethylphenylsiloxane, and polydiphenylsiloxane, among many others. Such polymers are commonly crosslinked.

In general, polyurethanes are a family of polymers that are synthesized from polyfunctional isocyanates (e.g., diisocyanates, including both aliphatic and aromatic diisocyanates) and polyols (also, referred to as macroglycols, e.g., macrodiols). Commonly employed macroglycols include polyester glycols, polyether glycols and polycarbonate glycols. Typically, aliphatic or aromatic diols are also employed as chain extenders, for example, to impart the useful physical properties. Examples of diol chain extenders include butane diol, pentane diol, hexane diol, heptane diol, benzene dimethanol, hydraquinone diethanol and ethylene glycol. Polyurethanes are commonly classified based on the type of macroglycol employed, with those containing polyester glycols being referred to as polyester polyurethanes, those containing polyether glycols being referred to as polyether polyurethanes, and those containing polycarbonate glycols being referred to as polycarbonate polyurethanes. Polyurethanes are also commonly designated as aromatic or aliphatic on the basis of the chemical nature of the diisocyanate component in their formulation. For example, U.S. Patent App. No. 2004/0131863 to Belliveau et al. describes aliphatic polycarbonate polyurethanes which are the reaction products of (a) a hydroxyl terminated polycarbonate, (b) an aliphatic diisocyanate and (c) a lower aliphatic chain extender. Hydroxyl terminated polycarbonate polyol may be prepared by reacting a glycol with a carbonate, as disclosed in U.S. Pat. No. 4,131,731. Suitable aliphatic diisocyanates include hexamethylene diisocyanate (HDI), isophorone diisocyanate (IPDI), trimethyl hexamethylene diisocyanate (TMHDI), dicyclohexyl methane diisocyanate (HMDI), and dimer acid diisocyanate (DDI), with HMDI said to be preferred. Suitable chain extenders include lower aliphatic glycols having from about 2 to about 10 carbon atoms, such as, for instance ethylene glycol, diethylene glycol, propylene glycol, dipropylene glycol, 1,4-butanediol, 1,6-hexanediol, 1,3-butanediol, 1,5-pentanediol, 1,4-cyclohexanedimethanol hydroquinone di(hydroxyethyl)ether, neopentyglycol, and the like, with 1,4-butanediol said to be preferred.

Another group of polymers are block copolymers comprising polyether blocks (i.e., polymer blocks containing multiple C—O—C linkages) and polyamide blocks (i.e., polymer blocks containing multiple —NH—CO— linkages), sometimes referred to as poly(ether-b-amides) or polyether-block-amides. A few specific examples of polyether blocks include homopolymeric and copolymeric blocks of the formulas (a) —[$R_1$—O—]$_n$— or (b) —[$R_1$—O—$R_2$—O]$_n$—, where $R_1$ and $R_2$ can be the same or different and may be selected from linear, branched and cyclic alkyl groups, aromatic groups and alky-aromatic groups, for example, having from 1 to 10 carbon atoms (more typically linear or branched alkyl groups having from 1 to 6 carbons) and where n is an integer of 5 or more, typically 10 to 25 to 50 to 100 to 250 to 500 to 1000 or more. Polyethers may be formed, for example, from ring opening addition polymerization of cyclic ethers, such as ethylene oxide, where $R_1$=$R_2$=dimethylene (i.e., [—(CH$_2$)$_2$—O—]$_n$), which is commonly referred to as polyethylene glycol or as polyethylene oxide), trimethylene oxide, where $R_1$=$R_2$=trimethylene (i.e., [—(CH$_2$)$_3$—O—]$_n$), propylene oxide, where $R_1$=$R_2$=methyl substituted dimethylene (i.e., [—CH$_2$CH$_2$(CH$_3$)—O—]$_n$, referred to as polypropylene glycol or polypropylene oxide), and tetrahydrofuran, where $R_1$=$R_2$=tetramethylene (i.e., —[(CH$_2$)$_4$—O]—$_n$, which is referred to as polytetramethylene glycol, polytetramethylene oxide (PTMO), or teratahane). Examples of polyamide blocks, which may be provided, for example, as homopolymeric or copolymeric blocks, include polyamides of the formula —[$R_3$—NH—CO]$_m$— or —[NH—$R_3$—NH—CO—$R_4$—CO]$_m$—, where $R_3$ and $R_4$ can be the same or different and may be selected from linear, branched and cyclic alkyl groups, aromatic groups and alky-aromatic groups, for example, of 1 to 20 carbon atoms (more typically linear or branched alkyl groups having from 1 to 15 carbons, such as methyl, ethyl, propyl, isopropyl, and so forth) and where m is an integer of 5 or more, typically 10 to 25 to 50 to 100 to 250 to 500 to 1000 or more. Specific examples include nylons, such as nylon 6, nylon 4/6, nylon 6/6, nylon 6/10, nylon 6/12, nylon 11 and nylon 12. A specific example of a polyether-polyamide block copolymer is poly(tetramethylene oxide)-b-polyamide-12 block copolymer, available from Elf Atochem as PEBAX.

Further polymers include polyalkene homopolymers and copolymers with themselves and with various other monomers including those selected from vinyl aromatic monomers such as styrene, acrylic acid, methacrylic acid, and vinyl acetate. Examples of alkene monomers include ethylene, propylene, isobutylene, 1-butene, 1-pentene, 4-methyl-1-pentene, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, among others. Specific examples of alkene copolymers include, poly(ethylene-co-vinyl acetate) (EVA), poly(ethylene-co-methacrylic acid), poly(ethylene-co-acrylic acid), and poly(isobutylene-co-styrene), among many others.

Poly(isobutylene-co-styrene) copolymers include poly (styrene-b-isobutylene-b-styrene) triblock copolymers (SIBS), which are described in U.S. Pat. No. 6,545,097 to Pinchuk et al. SIBS is a thermoplastic elastomer.

Among EVA copolymers are included random and other copolymers having a vinyl acetate weight percent ratio of from about 0.5% to 1% to 2% to 5% to 15% to 20% to 30% to 40% or more. In general, the higher the vinyl acetate content, the lower the stiffness and Durometer of the EVA and the higher the release rate of a given urologically beneficial agent. For example, EVA having a high vinyl acetate content (e.g., 25 to 35 wt % or more) may be employed in the kidney portion for increased release, while EVA having a low vinyl acetate content (e.g., 10 to 20 wt % or less) may be employed in the ureter and bladder portions for reduced release. As another example, EVA having a high vinyl acetate content (e.g., 25 to 35 wt % or more %) may be employed in the kidney portion for increased release, EVA having a low vinyl acetate content (e.g., 10 to 20 wt % or less) may be employed in the ureter portion for reduced release, and EVA having an intermediate vinyl acetate content (e.g., 20 to 25 wt %) may be employed in the bladder portion for intermediate release.

A wide range of agent loadings (e.g., selected from urologically beneficial agents, optional supplemental agents such as imaging agents, etc.) may be used in conjunction with the ureteral stents of the present invention, with the effective amount being readily determined by those of ordinary skill in the art. For a polymeric carrier region, typical loadings range, for example, from than 1 wt % or less to 2 wt % to 5 wt % to 10 wt % to 25 wt % to 50 wt % or more.

The release of the one or more urologically beneficial agents from the device will be affected by a number of variables. For example, for a given polymeric carrier region, the amount of urologically beneficial agent released will depend upon the particular agent(s) selected, the particular polymer(s) selected, and their relative amounts (i.e., agent loading). The amount of agent released may also be affected, for example, by the geometry (e.g., thickness and/or surface area) of the polymeric carrier region, among other factors.

In some embodiments, the amount of agent released may be increased by increasing the hydrophilicity of the carrier region, for example, by including a hydrophilic polymer or a polymeric with one or more hydrophilic polymer blocks in the carrier region. As another example, release may be increased by the addition of an osmotic agent such as a soluble salt or sugar excipient as an optional supplemental agent, and so forth.

Numerous techniques are available for forming polymeric carrier regions in accordance with the present invention.

For example, where the polymeric carrier region is formed from one or more polymers having thermoplastic characteristics, a variety of standard thermoplastic processing techniques may be used to form the polymeric carrier region, including injection molding, compression molding, blow molding, spinning, vacuum forming and calendaring, extrusion into sheets, fibers, rods, tubes and other cross-sectional profiles of various lengths, and combinations of these processes. Using these and other thermoplastic processing techniques, entire devices or portions thereof can be formed.

In some embodiments, mixing or compounding the one or more polymers and one or more agents (e.g., selected from urologically beneficial agents and optional supplemental agents) may be performed using any suitable processing technique known in the art. For example, where thermoplastic materials are employed, a polymer melt may be formed. A common way of doing so is to apply mechanical shear to a mixture of the polymer(s) and the agent(s). After compounding, the material may be processed using, for example, one or more of the thermoplastic techniques described above, among others.

Other processing techniques besides thermoplastic processing techniques may also be used to form the polymeric carrier regions of the present invention, including solvent-based techniques. Using these techniques, a polymeric carrier region can be formed by (a) first providing a solution or dispersion that contains (i) solvent, (ii) polymer(s), (iii) in some embodiments, urologically beneficial agent(s), and (iv) any optional supplemental agent(s), and (b) subsequently removing the solvent. The solvent that is ultimately selected will contain one or more solvent species (e.g., water and/or one or more organic solvents), which are generally selected based on their ability to dissolve the polymer(s) that form(s) the polymeric carrier region (and in many embodiments the urologically beneficial agent(s) and/or any optional supplemental agent(s)), in addition to other factors, including drying rate, surface tension, etc. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In certain embodiments of the invention, a polymer-containing solution (where solvent-based processing is employed) or a polymer melt (where thermoplastic processing is employed) is applied to a substrate to form a polymeric carrier region, which solution or melt may also contain urologically beneficial agent(s) and/or any optional supplemental agent(s). For example, the substrate can correspond to all or a portion of a ureteral stent body to which the polymeric carrier region is applied. The substrate can also be, for example, a template, such as a mold, from which the polymeric carrier region is removed after solidification. In certain other embodiments, for example, extrusion and co-extrusion techniques, one or more polymeric carrier regions are formed without the aid of a substrate. In a more specific example, an entire stent body may be extruded as a carrier region. In another, a polymeric carrier layer may be co-extruded along with an underlying stent body. In another, a polymeric carrier layer may be provided by spraying or extruding a coating layer onto a pre-existing stent body. In yet another more specific example, a stent body may be cast in a mold.

Coextrusion is a preferred process in some embodiments of the invention. For instance, coextrusion in accordance with the present invention may be based on the following: (a) a higher release composition containing a polymer and a urologically beneficial agent and (b) a lower release composition (which releases less urologically beneficial agent than the first composition, assuming samples of the same size and geometry, down to an including zero release, for instance, where no urologically beneficial agent is provided in the lower release composition). For example, the higher release composition may contain a polymer and a urologically beneficial agent in a first concentration and the lower release composition may contain the same polymer and urologically beneficial agent, but with the urologically beneficial agent in a lower concentration (down to and including 0%). As another example, the high release composition may contain a first polymer (e.g., higher vinyl acetate EVA, among many others) and a urologically beneficial agent and the lower release composition may contain a second polymer (e.g., lower vinyl acetate EVA, among many others) and the urologically beneficial agent. (As noted above, lower vinyl acetate EVA exhibits a lower release than does EVA having higher vinyl acetate content.)

In some embodiments, the kidney portion of the ureteral stent may be extruded using 100% of the higher release composition and the remainder of the stent may be extruded with 100% of the lower release composition.

The transition between higher and lower release compositions along the length of the stent may be gradual (e.g., by gradually increasing the relative amount of the lower release composition) or it may be abrupt. An abrupt transition may be created using interrupted layer co-extrusion (ILC), which is described, for example, in U.S. Pat. Nos. 5,622,665 and 6,508,805.

In other embodiments, the kidney portion of the ureteral stent may be extruded using 100% of the higher release composition and the remainder of the stent may be extruded with a blend of the higher and lower release compositions or 100% of the lower release composition. For example, the ureter portion of the stent may extruded with a first blend of the higher and lower release compositions, and the bladder portion of the stent may extruded with a second blend of the higher and lower release compositions, wherein the relative amount of the higher release composition in the second blend is higher than it is in the first blend. As another example, the ureter portion of the stent may extruded with 100% of the lower release composition, and the bladder portion of the stent may extruded with a blend of the higher and lower release compositions. Using these techniques, a ureteral stent may be formed in which the greatest release of urologically beneficial agent is from the kidney portion of the stent, the lowest release of urologically beneficial agent is from the ureter portion of the stent, and an intermediate release of urologically beneficial agent is from the bladder portion of the stent.

As seen from the above, where various agents—for example, urologically beneficial agent(s) and/or any optional supplemental agent(s)—are stable under the polymer processing conditions employed, then they can be combined with the polymer(s) and co-processed along with the same to form the polymeric carrier region of interest. Alternatively, the agent or agents of choice can be introduced subsequent to the formation of the polymeric region using techniques such as imbibing (e.g., where the agent or agents of choice are dissolved or dispersed in a solvent and then contacted with the device, for instance, by spraying, dipping, etc.).

Finally, at least one polymeric barrier layer may be provided over a carrier region in order to reduce release in certain embodiments of the invention. In these embodiments, the polymeric barrier layer may be formed over the carrier region, for example, using one of the solvent based or thermoplastic techniques described above. Alternatively, a previously formed polymeric barrier region may be adhered over a carrier region.

Various aspects of the invention relating to the above are enumerated in the following paragraphs:

Aspect 1. A ureteral stent comprising an elongated stent body and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, and said ureteral stent being adapted to release said first urologically beneficial agent such that at least 50% of the cumulative total release of first urologically beneficial agent that occurs during a period corresponding to the first 7 days of stent implantation is released from the kidney portion of the stent.

Aspect 2. The ureteral stent of aspect 1, wherein the first urologically beneficial agent is selected from alpha-adrenergic blockers, calcium channel blockers, beta-adrenergic agonists, bronchodilators, nitric oxide donors, nitric oxide releasing compounds, prostaglandins, corticosteroids, narcotic analgesic agents, non-narcotic analgesic agents, local anesthetic agents, antiproliferative agents and antineoplastic agents.

Aspect 3. The ureteral stent of aspect 1, wherein at least 75% of the cumulative total release of the first urologically beneficial agent is released from the kidney portion during said period.

Aspect 4. The ureteral stent of aspect 1, wherein at least 90% of the cumulative total release of the first urologically beneficial agent is released from the kidney portion during said period.

Aspect 5. The ureteral stent of aspect 1, wherein at least 95% of the cumulative total release of the first urologically beneficial agent is released from the kidney portion during said period.

Aspect 6. The ureteral stent of aspect 1, wherein a cumulative release of the first urologically beneficial agent from the bladder portion during said period is at least two times a cumulative release of the first urologically beneficial agent from the ureter portion during said period, and wherein a cumulative release of the first urologically beneficial agent from the kidney portion during said period is at least two times the cumulative release of the first urologically beneficial agent from the bladder portion during said period.

Aspect 7. The ureteral stent of aspect 1, wherein at least 75% of the total first urologically beneficial agent within the ureteral stent is located in the kidney portion.

Aspect 8. The ureteral stent of aspect 1, wherein at least 90% of the total first urologically beneficial agent within the ureteral stent is located in the kidney portion.

Aspect 9. The ureteral stent of aspect 1, wherein at least 95% of the total first urologically beneficial agent within the ureteral stent is located in the kidney portion.

Aspect 10. The ureteral stent of aspect 1, wherein the amount of the first urologically beneficial agent in the bladder portion is at least two times the amount of the first urologically beneficial agent in the ureter portion and wherein the amount of the first urologically beneficial agent in the kidney portion is at least two times the amount of the first urologically beneficial agent in the bladder portion.

Aspect 11. The ureteral stent of aspect 1, wherein the kidney portion comprises a first carrier region comprising said first urologically beneficial agent and a first polymer.

Aspect 12. The ureteral stent of aspect 11, wherein the first polymer is selected from polycarbonates, silicone polymers, polyurethanes, poly(ether-block-amides), and alkene copolymers.

Aspect 13. The ureteral stent of aspect 11, wherein the bladder portion comprises a second carrier region comprising said first urologically beneficial agent and a second polymer, wherein the ureter portion comprises a third carrier region comprising said first urologically beneficial agent and a third polymer, and wherein the first, second and third polymers may be the same or different.

Aspect 14. The ureteral stent of aspect 13, wherein the first, second and third polymers are selected from polycarbonates, silicone polymers, polyurethanes, poly(ether-block-amides), and alkene copolymers.

Aspect 15. The ureteral stent of aspect 14, wherein the first polymer comprises EVA having a first vinyl acetate content, wherein the second polymer comprises EVA having a second vinyl acetate content, wherein the third polymer comprises EVA having a third vinyl acetate content, wherein the first vinyl acetate content is higher than the second vinyl acetate content, and wherein the second vinyl acetate content is higher than the third vinyl acetate content.

Aspect 16. The ureteral stent of aspect 11, wherein the ureter portion comprises a polymeric region comprising a second polymer, wherein the bladder portion comprises a polymeric region comprising a third polymer, and wherein the first, second and third polymers may be the same or different.

Aspect 17. The ureteral stent of aspect 1, wherein the kidney and bladder portions each comprise coiled retention structures.

Aspect 18. The ureteral stent of aspect 1, further comprising a second urologically beneficial agent that is different from the first urologically beneficial agent, said ureteral stent being adapted to release said second urologically beneficial agent such that at least 50% of the cumulative total release of said second urologically beneficial agent that occurs during said period of stent implantation is released from the kidney portion of the stent.

Aspect 19. The ureteral stent of aspect 18, wherein the first urologically beneficial agent is a pain relief agent and wherein the second urologically beneficial agent is an anticancer agent.

Aspect 20. A ureteral stent comprising an elongated stent body and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein at least 50% of the total amount of the first urologically beneficial agent within the ureteral stent is located in the kidney portion of the stent.

Aspect 21. The ureteral stent of aspect 20, wherein an amount of the first urologically beneficial agent located in the bladder portion is at least two times an amount of the first urologically beneficial agent located in the ureter portion and wherein the amount of the first urologically beneficial agent located in the kidney portion is at least two times the amount of the first urologically beneficial agent located in the bladder portion.

Aspect 22. The ureteral stent of aspect 20 wherein a concentration of the first urologically beneficial agent in the bladder portion is at least two times a concentration of the urologically beneficial agent in the ureter portion, and wherein a concentration of the first urologically beneficial agent in the kidney portion is at least two times the concentration of the first urologically beneficial agent in the bladder portion.

Aspect 23. A ureteral stent comprising an elongated stent body and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein an amount of the first urologically beneficial agent located in the kidney portion is at least two times the amount of the first urologically beneficial agent located in the ureter portion.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A ureteral stent comprising an elongated stent body comprised of a solid polymeric composition comprising a polymer and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein said ureter portion constitutes 60-80% of the length of the stent, wherein said ureteral stent is adapted to release said first urologically beneficial agent such that said kidney portion has a higher cumulative total release of said first urologically beneficial agent during the first 7 days of implantation than does the remainder of the stent, wherein a cumulative release of said first urologically beneficial agent from the bladder portion during the first 7 days of implantation is at least two times a cumulative release of said first urologically beneficial agent from the ureter portion during the first 7 days of implantation, and wherein a cumulative release of the first urologically beneficial agent from the kidney portion during the first 7 days of implantation is at least two times the cumulative release of the first urologically beneficial agent from the bladder portion during the first 7 days of implantation.

2. The ureteral stent of claim 1, wherein said first urologically beneficial agent is selected from alpha-adrenergic blockers, calcium channel blockers, beta-adrenergic agonists, bronchodilators, nitric oxide donors, nitric oxide releasing compounds, pro staglandins, corticosteroids, narcotic analgesic agents, non-narcotic analgesic agents, local anesthetic agents, antiproliferative agents and antineoplastic agents.

3. The ureteral stent of claim 1, wherein at least 75% of the cumulative total release of said first urologically beneficial agent is released from the kidney portion during the first 7 days of implantation.

4. The ureteral stent of claim 1, wherein at least 90% of the cumulative total release of said first urologically beneficial agent is released from the kidney portion during the first 7 days of implantation.

5. The ureteral stent of claim 1, wherein at least 95% of the cumulative total release of said first urologically beneficial agent is released from the kidney portion during the first 7 days of implantation.

6. The ureteral stent of claim 1, wherein at least 75% of a total amount of the first urologically beneficial agent within the ureteral stent is located in the kidney portion.

7. The ureteral stent of claim 1, wherein at least 90% of a total amount of the first urologically beneficial agent within the ureteral stent is located in the kidney portion.

8. The ureteral stent of claim 1, wherein at least 95% of a total amount of the first urologically beneficial agent within the ureteral stent is located in the kidney portion.

9. The ureteral stent of claim 1, wherein said kidney portion comprises a first carrier region comprising said first urologically beneficial agent and a first polymer.

10. The ureteral stent of claim 9, wherein said first polymer is selected from polycarbonates, silicone polymers, polyurethanes, poly(ether-block-amides), and alkene copolymers.

11. The ureteral stent of claim 9, wherein said bladder portion comprises a second carrier region comprising said first urologically beneficial agent and a second polymer, wherein the ureter portion comprises a third carrier region comprising said first urologically beneficial agent and a third polymer, and wherein the first, second and third polymers are the same or different.

12. The ureteral stent of claim 11, wherein said first, second and third polymers are selected from polycarbonates, silicone polymers, polyurethanes, poly(ether-block-amides), and alkene copolymers.

13. The ureteral stent of claim 12, wherein said first polymer comprises EVA having a first vinyl acetate content, wherein said second polymer comprises EVA having a second vinyl acetate content, wherein said third polymer comprises EVA having a third vinyl acetate content, wherein said first vinyl acetate content is higher than said second vinyl acetate content, and wherein said second vinyl acetate content is higher than said third vinyl acetate content.

14. The ureteral stent of claim 9, wherein said ureter portion comprises a polymeric region comprising a second polymer, wherein said bladder portion comprises a polymeric region comprising a third polymer, and wherein said first, second and third polymers are the same or different.

15. The ureteral stent of claim 1, wherein said kidney and bladder portions each comprise coiled retention structures.

16. The ureteral stent of claim 1, further comprising a second urologically beneficial agent that is different from said first urologically beneficial agent, said ureteral stent being adapted to release said second urologically beneficial agent such that at least 50% of the cumulative total release of said second urologically beneficial agent that occurs during the first 7 days implantation is released from the kidney portion of the stent.

17. The ureteral stent of claim 16, wherein said first urologically beneficial agent is a pain relief agent and wherein said second urologically beneficial agent is an anti-cancer agent.

18. A ureteral stent comprising an elongated stent body comprised of a solid polymeric composition comprising a polymer and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein said ureter portion constitutes 60-80% of the length of the stent, wherein said ureteral stent is adapted to release said first urologically beneficial agent such that said kidney portion has a higher cumulative total release of said first urologically beneficial agent during the first 7 days of implantation than does the remainder of the stent, wherein an amount of said first urologically beneficial agent in the bladder portion is at least two times an amount of said first urologically beneficial agent in the ureter portion and wherein an amount of said first urologically beneficial agent in the kidney portion is at least two times the amount of said first urologically beneficial agent in the bladder portion.

19. A ureteral stent comprising an elongated stent body and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein the ureter portion constitutes 60-80% of the length of the stent, wherein at least 50% of a total amount of said first urologically beneficial agent within the ureteral stent is located in the kidney portion of the stent, and (a) wherein an amount of said first urologically beneficial agent located in the bladder portion is at least two times an amount of said first urologically beneficial agent located in the ureter portion and an amount of said first urologically beneficial agent located in the kidney portion is at least two times the amount of said first urologically beneficial agent located in the bladder portion or (b) wherein a concentration of said first urologically beneficial agent in the bladder portion is at least two times a concentration of said first urologically beneficial agent in the ureter portion, and wherein a concentration of said first urologically beneficial agent in the kidney portion is at least two times the concentration of said first urologically beneficial agent in the bladder portion.

20. The ureteral stent of claim 19, wherein the amount of said first urologically beneficial agent located in the bladder portion is at least two times the amount of said first urologically beneficial agent located in the ureter portion and wherein the amount of said first urologically beneficial agent located in the kidney portion is at least two times the amount of said first urologically beneficial agent located in the bladder portion.

21. The ureteral stent of claim 19 wherein the concentration of said first urologically beneficial agent in the bladder portion is at least two times the concentration of said first urologically beneficial agent in the ureter portion, and wherein the concentration of said first urologically beneficial agent in the kidney portion is at least two times the concentration of said first urologically beneficial agent in the bladder portion.

22. A ureteral stent comprising an elongated stent body comprised of a solid polymeric composition containing a polymer and a first urologically beneficial agent, said elongated stent body comprising a kidney portion adapted to occupy the kidney upon implantation, a ureter portion adapted to occupy the ureter upon implantation, and a bladder portion adapted to occupy the bladder upon implantation, wherein the ureter portion constitutes 60-80% of the length of the stent and (a) wherein an amount of said first urologically beneficial agent located in the bladder portion is at least two times an amount of said first urologically beneficial agent located in the ureter portion and an amount of said first urologically beneficial agent located in the kidney portion is at least two times the amount of said first urologically beneficial agent located in the bladder portion or (b) wherein a concentration of said first urologically beneficial agent in the bladder portion is at least two times a concentration of said first urologically beneficial agent in the ureter portion, and wherein a concentration of said first urologically beneficial agent in the kidney portion is at least two times the concentration of said first urologically beneficial agent in the bladder portion.

* * * * *